(12) United States Patent
Henke

(10) Patent No.: US 7,282,039 B2
(45) Date of Patent: Oct. 16, 2007

(54) DEVICE FOR SELF ADMINISTRATION OF LUMBAR TRACTION

(76) Inventor: David E. Henke, 17803 E. Indian Ave., Greenacres, WA (US) 99016

( * ) Notice: Subject to any disclaimer, the term of this patent is extended or adjusted under 35 U.S.C. 154(b) by 369 days.

(21) Appl. No.: 11/036,020

(22) Filed: Jan. 18, 2005

(65) Prior Publication Data

US 2006/0161084 A1   Jul. 20, 2006

(51) Int. Cl.
*A61F 5/00* (2006.01)
(52) U.S. Cl. .............. 602/36; 602/32; 602/33; 602/34
(58) Field of Classification Search ............ 602/19, 602/32–36; 128/96.1, 98.1, 99.1, 101.1
See application file for complete search history.

(56) References Cited

U.S. PATENT DOCUMENTS 3,797,483 A * 3/1974 Feldman ............... 602/36
4,865,022 A * 9/1989 Gorsen ................. 602/33
5,242,380 A * 9/1993 Steinbrueck ........... 602/32
5,478,307 A * 12/1995 Wang ................... 602/32

* cited by examiner

*Primary Examiner*—Kim M. Lewis
(74) *Attorney, Agent, or Firm*—Keith S. Bergman; Willam A. Jeckle

(57) ABSTRACT

A device is disclosed for self administration of adjustable lumbar traction by a user in a supine position upon a support. The device comprises an upper body harness releasably encircling the torso and anchored to the support spacedly outwardly of the user's head, a lower body harness releasably encircling the user's waist and anchored to a support spacedly outwardly of the user's feet and user adjustable elastically biased tensioning members extending between the lower body harness and the support to which it is anchored. The device is preferably carried on a bedstead or table.

3 Claims, 4 Drawing Sheets

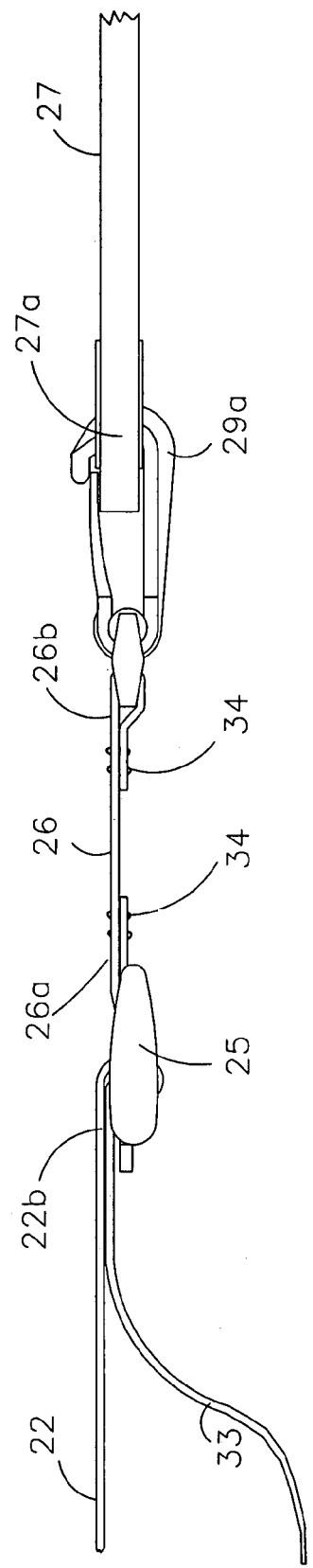
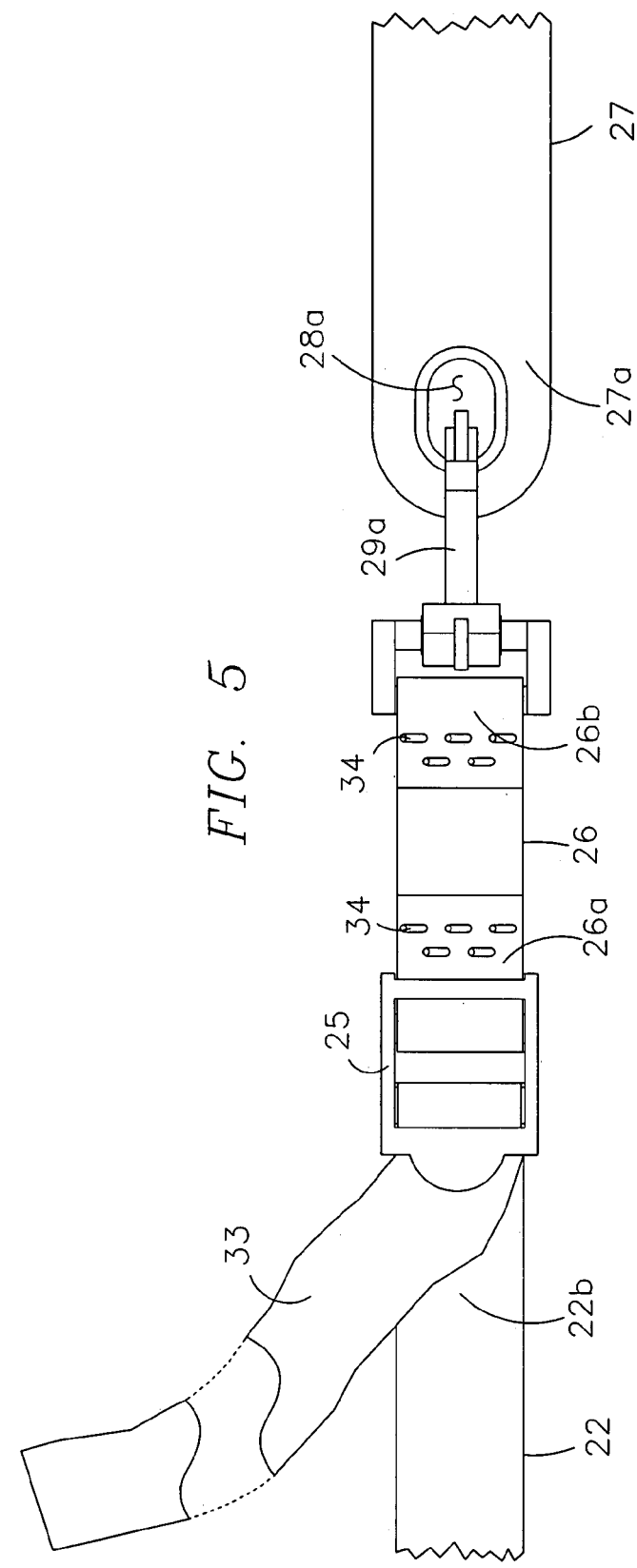

DEVICE FOR SELF ADMINISTRATION OF LUMBAR TRACTION

BACKGROUND OF INVENTION

Related Applications

There are no applications related hereto heretofore filed in this or in any foreign country.

Field of Invention

This invention relates to traction apparatus, and more particularly to a bedstead associated apparatus for self administration of lumbar traction in a supine position.

IIC. Background and Description of Prior Art

Lower back problems, including pain and stiffness, are common forms of disability in humans that may be caused by disease, injury, genetic predisposition, aging or otherwise. Treatments for lower back problems range from topical ointments to surgical fusion of vertebrae and excision of disks. Between these extremes are a myriad of treatments and devices for alleviation of pain and stiffness. One recognized method to alleviate pain and stiffness in the lumbar spine is application of traction. Most known lumbar traction devices however are complicated, motorized, or non-transportable and may require athletic ability and flexibility or the presence of an assistant.

One common lumbar traction device is a compound mechanical bed wherein a headboard portion and a footboard portion of the mattress move in opposite directions while a user is secured to the mattress portions so that movement of the mattress portions applies traction to a user's lumbar spine. Mechanical beds however are generally expensive and are only practical in hospital or other professional treatment environments.

Another common device for lumbar traction is known as "gravity boots". Gravity boots are bands releasably secured about a user's ankles with each band carrying a generally "U" shaped appendage to suspend a user in an inverted position from a suspension bar. Gravity acting upon an inverted user then tends to stretch the lumbar spine. Proper use of gravity boots however requires the user to have some athletic ability, strength, coordination, and dexterity all of which may be diminished by the lower back problems giving rise to the need for lumbar traction. The use of gravity boots may require the assistance of a second party or may be used in conjunction with mechanical apparatus, generally an inversion table, that moves the user from a supine position to a suspended inverted position without requiring the user to perform physically demanding athletic maneuvers. Inversion tables are large, complicated, immobile and expensive as well as having inherent risks of injury to the user.

There remains a need for a device that enables safe self administration of lumbar traction, is transportable, may be manipulated by the user alone, and does not require athletic ability to use.

The instant invention seeks to provide such a device and is distinguishable from the prior art by its simple construction, provision of lumbar traction while a user is in a supine position and small size that allows easy transportability.

My invention does not reside in any of the foregoing features individually but rather in the synergistic combination of all of its structures, which necessarily give rise to the functions flowing therefrom as herein specified and claimed.

SUMMARY OF THE INVENTION

A device for self administration of lumbar traction by a supine user provides an upper body harness encircling the chest and a lower body harness encircling the waist, both body harnesses being formed of flexible straps having buckles interconnecting strap portions to allow size adjustment of each harness.

The upper body harness is releasably interconnected to an upper body harness anchor immovably supported spacedly outwardly from a user's head. The lower body harness releasably carries similar opposed side straps, each having a buckle for length adjustment, that each interconnect an elongate elastic tensioning member. Each tensioning member interconnects an anchor connecting strap that extends to releasable interconnection with a crossmember supported by the vertical leg of the lower body harness anchor, which is immovably supported spacedly outwardly from the user's feet. Conveniently, but not necessarily, in using the device a user may be supported on a bed and both body harness anchors may be "L" shaped members having longer horizontal legs supported beneath the bed mattress, with shorter vertical legs projecting upwardly spacedly above the mattress for interconnection with the respective associated body harness.

In providing such a device it is:

A principal object to provide a device that permits self application of traction to the lumbar spine while the user is in a supine position as on a bed or similar support.

A further object is to provide such a device wherein the amount of traction being applied is adjustable by the user while using the device.

A further object is to provide such a device that is of relatively small compact configuration to make it readily transportable.

A still further object is to provide such a lumbar traction device that is of new and novel design, of a rugged and durable nature, of simple and economic manufacture and one that is otherwise well suited to the uses and purposes for which it is intended.

BRIEF DESCRIPTIONS OF DRAWINGS

In the accompanying drawings which form a part hereof and wherein like numbers of references refer to similar parts throughout:

FIG. 4 is an enlarged orthographic plan view of the interconnection of the right side connecting strap with the right side elastic tensioning member.

FIG. 5 is an enlarged orthographic side view of the interconnection of the right side connecting strap with the right side elastic tensioning strap illustrated in FIG. 4.

DESCRIPTION OF THE PREFERRED EMBODIMENT

Figure 1:
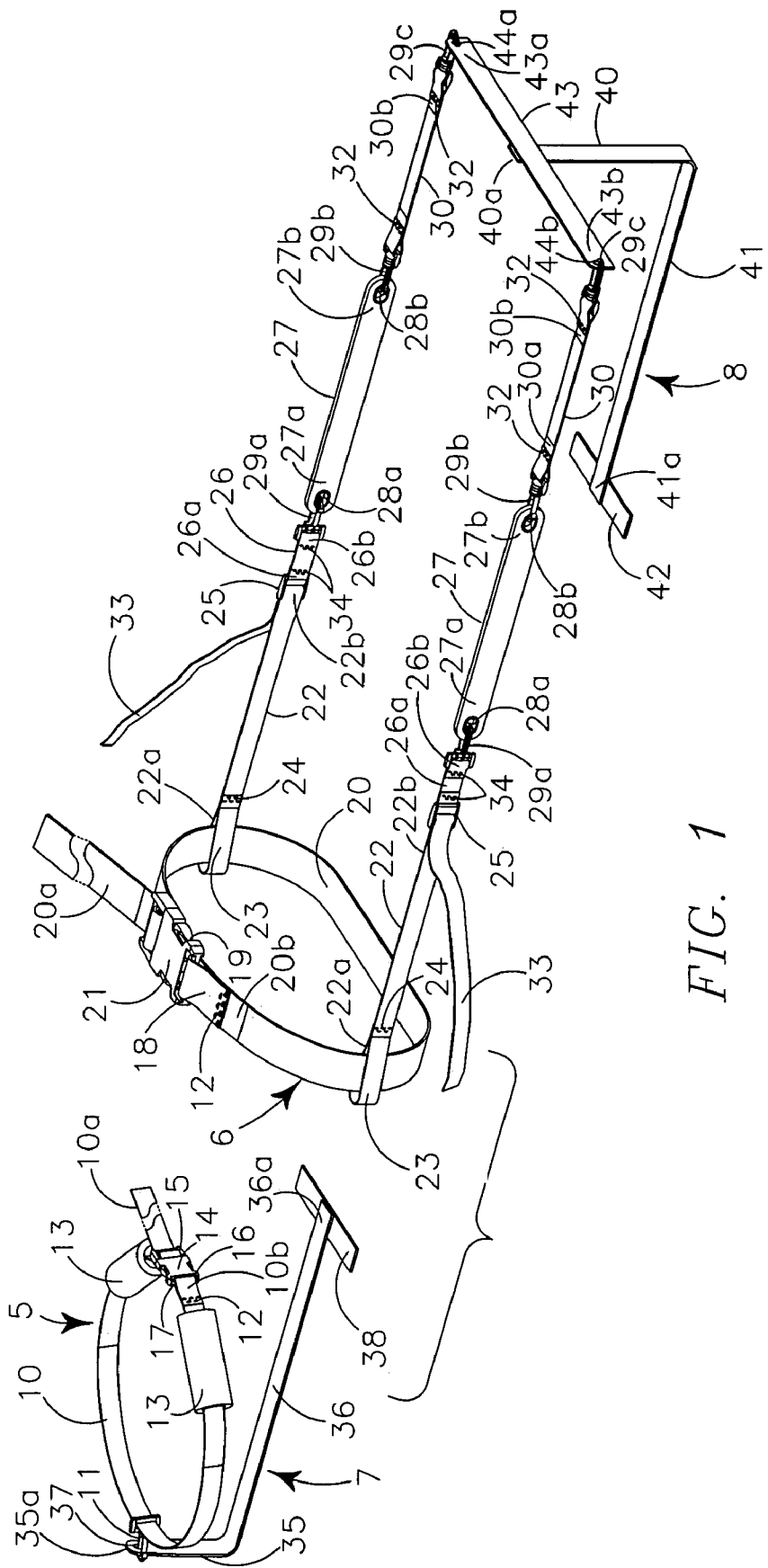
FIG. 1 is an isometric right side view of my lumbar traction device showing the upper body harness connected to the upper body harness anchor, and the lower body harness connected to the lower body harness anchor in operative orientation to one another.

My traction device generally provides upper body harness 5 and lower body harness 6 fastened to an external support by upper body harness anchor 7 and lower body harness anchor 8, which in a species may take the form of upper body harness fastening bracket 50 and lower body harness fastening bracket 70 respectively.

As shown in FIG. 1, upper body harness anchor 7 is a rigid "L" shaped member having a first end portion 35a at the outer end of vertical leg 35 and a second end portion 36a at the outer end of horizontal leg 36. An anti-rotation crossmember 38 is structurally carried to extend perpendicularly to horizontal leg 36 adjacent the second end portion 36a. Orifice 37 is defined in first end portion 35a of vertical leg 35 and is sized to carry releasable anchor connector 11 to interconnect upper body harness 5 to upper body harness anchor 7. The upper body harness 5 is comprised of chest encircling strap 10 having first end portion 10a and second end portion 10b. Chest encircling strap 10 carries in its medial portion releasable anchor connector 11 and two adjustably positionable armpit pads 13. The chest encircling strap 10 carries at its second end portion 10b compound buckle 14 having interlocking male portion 15 and female portion 16. The female portion 16 of compound buckle 14 is carried at second end portion 10b of chest encircling strap 10 by a loop formed by folding the second end portion 10b of strap 10 over onto itself and securing the loop in place by stitching 12. The male portion 15 of the compound buckle 14 is carried on strap 10 at the first end portion 10a. The compound buckle 14 is positionable over the chest of the user.

The lower body harness 6 shown in FIG. 1 is comprised of belt 20 having first end portion 20a and second end portion 20b carrying belt buckle 21 of known construction. Belt buckle 21 is secured at the second end portion 20b of belt 20 with a loop formed by passing second end portion 20b through orifice 19 in belt buckle 21 and thereafter folding the second end portion 20b over onto itself and securing the second end portion 20b in place by stitching 12. Belt buckle 21 receives first end portion 20a of belt 20 in a releasably fastenable interconnection to permit length adjustability and secure the belt 20 about the user's waist. Two elongate side straps 22 each having first upper end portions 22a and second lower end portions 22b extend from belt 20. A loop formed in the first upper end portion 22a of side strap 22 carries belt 20. The loop is formed by folding the first upper end portion 22a over itself and securing the endmost portion in place with stitching 24. A side strap buckle 25 is carried on each side strap 22 at a somewhat medial position and is movable along the length of the side strap 22.

As shown in FIGS. 4 and 5, connecting straps 26 having first upper end portions 26a and second lower end portions 26b depend from each side strap buckle 25. Connecting strap 26 is secured to side strap buckle 25 by passing upper end portion 26a through buckle 25 and folding the end portion 26a back upon itself to form a loop that is secured in place by stitching 34. Connecting straps 26 carry at their second lower end portions 26b releasable snap connectors 29a in a loop formed similarly to the loop in the first end portions 26a of connecting straps 26.

Snap connector 29a releasably engages in orifice 28a defined in first upper end portion 27a of elastic tensioning member 27 which also has a second lower end portion 27b defining orifice 28b.

Figure 2:
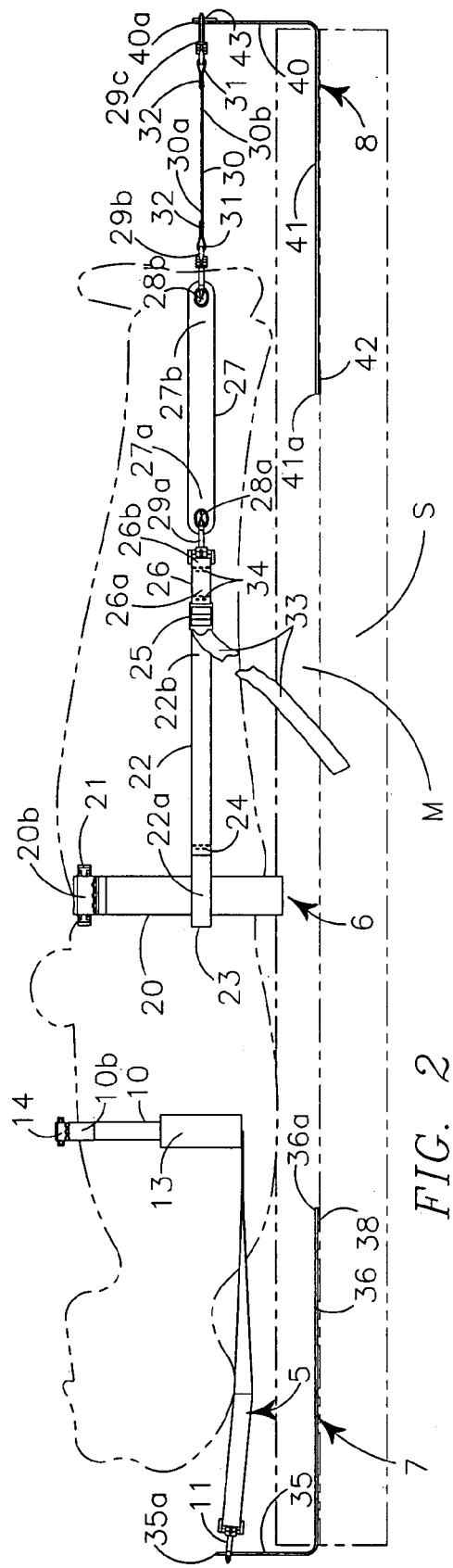
FIG. 2 is an orthographic right side view of a supine figure in phantom outline using the instant device for lumbar traction.
Figure 3:
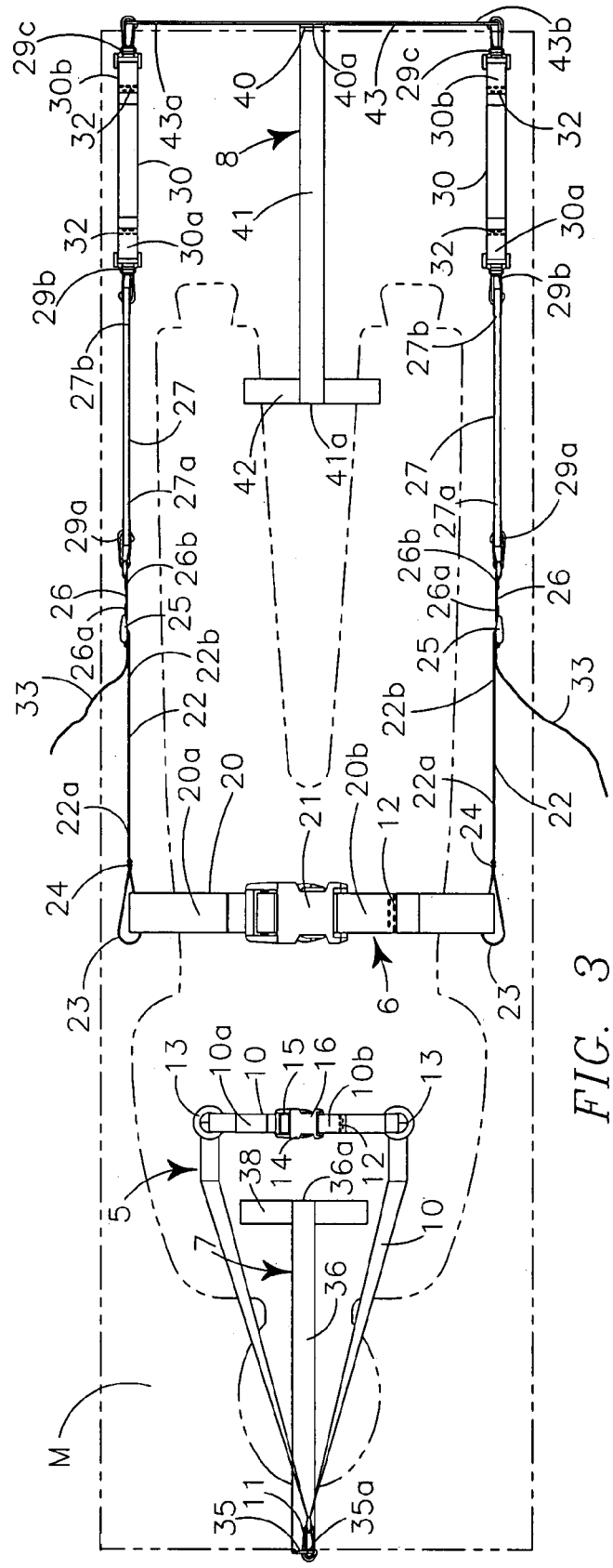
FIG. 3 is an orthographic plan view of the device of FIG. 2.

As shown in FIGS. 2 and 3 orifice 28b of elastic tensioning member 27 carries releasable snap connector 29b which is carried at first upper end portion 30a of anchor connecting strap 30 in a loop formed in the upper end portion 30a and secured by stitching 32. Anchor connecting strap 30 carries at its second lower end portion 30b releasable snap connector 29c in a loop formed in the second lower end portion 30b and secured in place by stitching 32. Releasable snap connector 29c fastens to lower body harness anchor 8.

As shown in FIG. 3 side strap 22 is elongate and has excess length 33 so that after passing through side strap buckle 25 the excess length 33 is oriented upwardly toward belt 20 where it is within reach of a user's hands while user is supine.

As shown in FIG. 1, the lower body harness anchor 8 is a rigid "L" shaped member having first end portion 40a at the outer end of vertical leg 40 and a second end portion 41a at the outer end of horizontal leg 41. An anti-rotation crossmember 42 is structurally fastened to horizontal leg 41 to extend perpendicularly therefrom adjacent second end 41a. Anchor strap crossmember 43 having first end portion 43a defining orifice 44a and second end portion 43b defining orifice 44b is structurally attached in its medial portion to the first end portion 40a of vertical leg 40 and extends parallel to the anti-rotation crossmember 42. Orifices 44a and 44b provide connection points for releasable snap connectors 29c.

Figures 6, 7:
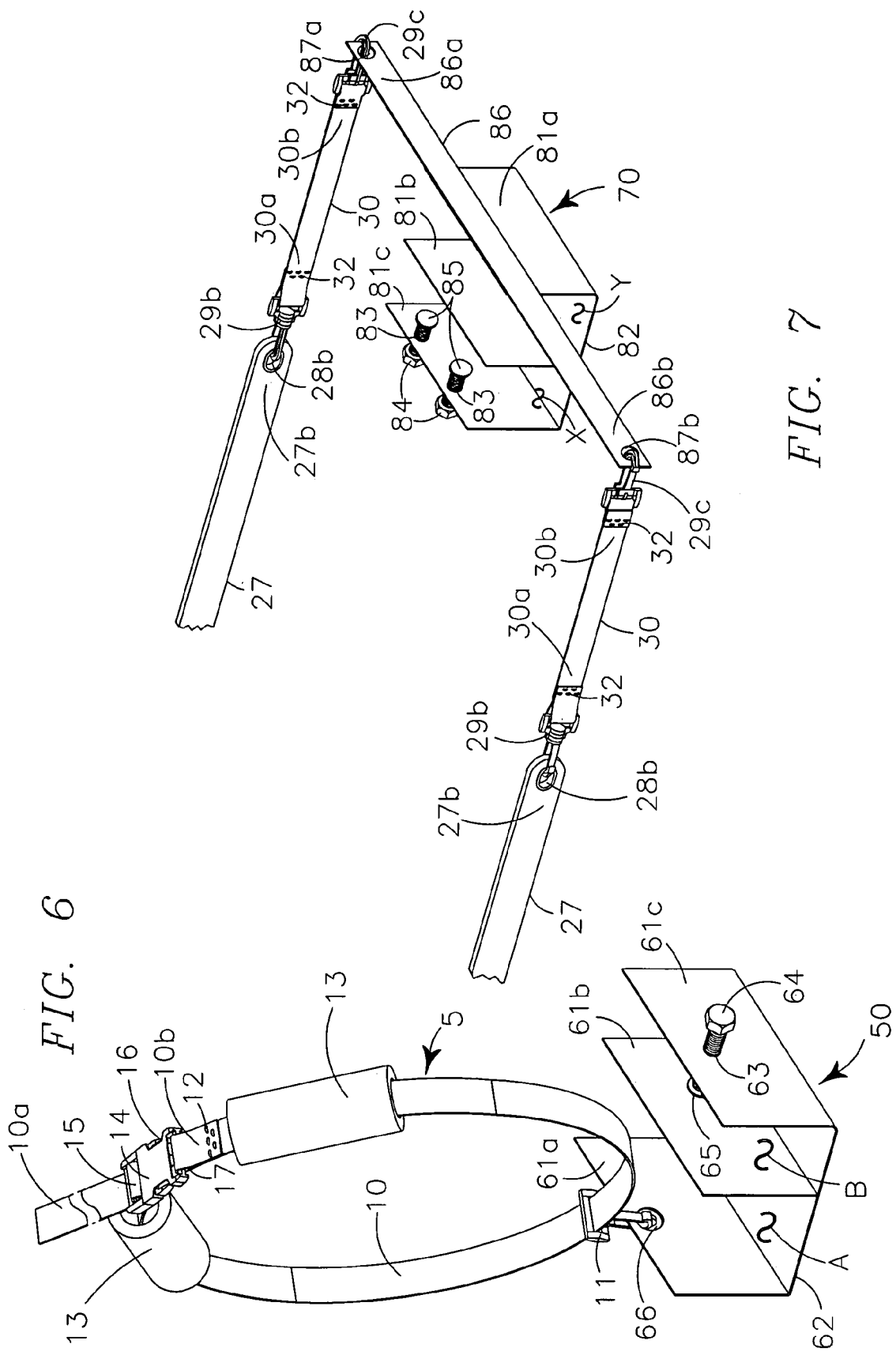
FIG. 6 is an enlarged isometric view of an upper body harness fastening bracket configured for releasable connection to a treatment or examination table.
FIG. 7 is an enlarged isometric view of a lower body harness fastening bracket configured for releasable connection to a treatment or examination table.

FIGS. 6 and 7 show a second species of means for securing my invention to a user support such as a treatment or examination table. The upper body harness fastening bracket 50 is comprised of three similar parallel rectilinear plates 61a, 61b, 61c. Rectilinear plates 61a, 61b, 61c are spacedly adjacent one another and are structurally secured at a first edge to a perpendicular base plate 62 forming two parallel adjacent channels designated A and B. Two orifices 63 having threads on theirs internal circumferential surfaces are defined in rectilinear plate 61c in generally medial positions therein to carry threaded securing bolts 64 therein to extend into channel B. End piece 65 having a disk shape is carried at the outer end portion of each threaded securing bolt 64 after positioning within channel B. Orifice 66 is defined in rectilinear plate 61a medially between the lateral sides and spacedly adjacent the second edge for engagement with releasable anchor connector 11 carried by chest encircling strap 10.

Lower body harness fastening bracket 70 is comprised of three similar parallel rectilinear plates 81a, 81b, 81c spacedly adjacent one another and structurally secured at a first edges to perpendicular base plate 82 forming two parallel adjacent channels designated X and Y. Plural horizontally aligned spaced orifices 83 are defined in rectilinear plate 81c in a generally medial positions. Each orifice 83 defines threads on its internal circumferential surface for engagement with threaded securing bolts 84 carried therein to extend into channel X. End pieces 85 having a disk shape are carried at the outer end portions of each threaded securing bolt 84 after positioning within channel X.

Fastening bracket crossmember 86, having first end portion 86a defining orifice 87a and second end portion 86b defining orifice 87b, is structurally attached to rectilinear plate 81a along the upper edge opposite perpendicular base plate 82 and extends parallel to channel Y. Orifices 87a and 87b receive releasable snap connectors 29c of anchor connecting straps 30.

Having described the structure of my traction device its operation and use may be understood.

Upper body harness anchor 7 may be installed by placing the horizontal leg 36 between a box spring S and a mattress M at a first end of a bed formed thereby with vertical leg 35 oriented upwardly and adjacent the first vertical end of the mattress M. The lower body harness anchor 8 is positioned similarly between the box spring S and mattress M at the second end of the bed opposite the upper body harness anchor 7. The upper body harness 5 is interconnected to the upper body harness anchor 7 by engaging releasable anchor connector 11 through orifice 37 defined in the first end portion 35a of vertical leg 35 of the upper body harness anchor 7. The first end portion 10a and second end portion 10b of the chest encircling strap 10 respectively carrying the male portion 15 and female portion 16 of the compound buckle 14 are positioned to extend toward the previously positioned lower body harness anchor 8.

Belt 20 of the lower body harness 6 is placed around the user's waist and secured in place with belt buckle 21. Side straps 22 depend from belt 20 adjacent each of the user's hips and each interconnects side strap buckle 25, connecting strap 26, elastic tensioning member 27, and anchor connecting strap 30 in the recited order.

The user sits on the mattress M, between the previously positioned upper body harness anchor 7 and lower body harness anchor 8 with feet proximate to the lower body harness anchor 8 and connects the releasable snap connectors 29c through orifices 44a and 44b defined in the first end portion 43a and second end portion 43b of anchor strap crossbar 43.

The user reclines to a supine position and second end portion 10b of the chest encircling strap 10 carrying the female portion 16 of compound buckle 14 is positioned under the left arm pit, and the first end portion 10a carrying the male portion 15 of the compound buckle 14 is place under the right arm pit. The male portion 15 of compound buckle 14 is inserted into the female portion 16 to fasten the chest encircling strap 10 about the user's chest. Fit and position of the chest encircling strap 10 may be adjusted by pulling on the first end portion 10a of the chest encircling strap 10. Arm pit pads 13 are positioned as desired by user for comfort.

While supine, the user grasps the excess length 33 of side straps 22 and by pulling the excess length 33 upwardly toward the user's chest draws a medial portion of side straps 22 through side strap buckles 25. Responsive to the decreased length of side straps 22 extending between belt 20 and connecting strap 26, the elastic tensioning straps 27 are stretched. The elasticity of tensioning members 27 pulls belt 20 secured about the user's waist toward the lower body harness anchor 8 applying traction primarily to the user's lumbar spine.

When a user wishes to discontinue the traction he or she may release the tension by disrupting the parallel alignment of the side strap buckles 25 with the side straps 22 and connecting straps 26. Alternatively, tension may be released by disconnecting the belt buckle 21, or by disengaging the male portion 15 from the female portion 16 of the compound buckle 14.

In the preferred embodiment all straps and belt elements are formed of nylon strapping, however alternative materials may be used such as other natural or artificial fiber, leather, rubber or the like. Further, in my preferred embodiment the elastic tensioning members are a "bungee type" rubber strap, however alternative elastically biasing devices may be used, such as springs (or the like).

The foregoing description of my invention is necessarily of a detailed nature so that a specific embodiment of its best known mode may be set forth, as is required, but it is to be understood that various modifications of details, rearrangement and multiplication of parts may be resorted to without departing from its spirit, essence or scope.

Having thusly described my invention, what I desire to protect by Letters Patent, and

What I claim is:

1. A device releasably securable to a user body support for self administration of spinal traction to a supine user, comprising in combination:
    (a) an upper body harness having an elongate chest encircling strap with first and second opposed ends, the chest encircling strap carrying a compound buckle for releasably adjustably securing the ends of the chest encircling strap together about the user's torso and a releasable anchor connector;
    (b) a lower body harness having
        a belt with first and second ends each carrying a portion of a belt buckle for releasably adjustably securing the ends together with the belt about the user's waist,
        two side straps carried by and extending from the belt, each side strap having a first upper end portion defining a first loop carrying the belt, a second lower end portion with a side strap buckle immovably carried at a medial position and the second lower end portion extending upwardly upon itself through and beyond the side strap buckle,
        a connecting strap, having a first upper end portion and a second lower end portion, depending from interconnection with each side strap buckle and carrying a releasable snap connector in the second lower end portion,
        an elastic tensioning member depending from the connecting strap and having a first upper end portion defining an orifice engaged with the releasable snap connector of the connecting strap and a second lower end portion defining an orifice carrying a releasable snap connector,
        an anchor connecting strap depending from the elastic tensioning member and having a first upper end portion defining a loop carrying the releasable snap connector engaged with the orifice defined in the second lower end portion of the elastic tensioning member and a second lower end portion defining a loop carrying a releasable snap connector,
    (c) means carried at the second lower end portions of the anchor connecting straps for anchoring the lower body harness to a support outwardly of a user's feet to adjustably restrain movement of the lower body harness; and
    (d) means engagable with the releasable anchor connector carried by the chest encircling strap for anchoring the upper body harness to a support outwardly of the user's head to prevent movement of the upper body harness.

2. The device of claim 1 for use with a bed type body support wherein:
    the means for anchoring the lower body harness to the body support outwardly of the user's feet comprises an "L" shaped bracket having a vertical leg with a first outer end portion carrying a perpendicular anchor strap crossmember and a horizontal leg with a second outer end portion carrying an anti-rotation crossmember, the anchor strap crossmember having opposed end portions each defining an orifice to engage one of the releasable snap connectors carried by the anchor connecting straps; and the means for anchoring the upper body harness to the body support outwardly of the user's head is an "L" shaped bracket having a vertical leg with a first outer end portion defining an orifice to engage with the releasable anchor connector of the chest encircling strap and a horizontal leg having a second outer end portion carrying an anti-rotation crossmember.

3. The device of claim 1 for use with a table type body support wherein:

the means for anchoring the lower body harness to the body support outwardly of the user's feet is a fastening bracket, comprising;
  (a) three spacedly adjacent parallel plates each structurally fastened along a first edge to a perpendicular base plate to form two parallel channels between the plates with a first outward plate defining plural medially positioned horizontally spaced threaded orifices, defining,
  (b) threaded securing bolts carried in the threaded orifices to extend into the channel partially defined by the first outward plate,
  (c) a fastening bracket crossmember structurally carried by the edge of the outer vertical plate not carrying the threaded securing bolts to extend parallel to the carrying plate, the fastening bracket crossmember having opposed end portions defining orifices to engage one of the releasable snap connectors carried by the anchor connecting straps; and the means for anchoring the upper body harness to the body support is a fastening bracket comprising;
  (a) three spacedly adjacent parallel plates each structurally fastened along a first edge to a perpendicular base plate to form two parallel channels between the plates with a first outward plate defining at least one elongately medially positioned threaded orifice,
  (b) at least one threaded securing bolt carried in the at least one threaded orifice and extending into the channel partially defined by the first outward plate, and
  (c) an orifice defined in the outer plate not carrying the at least one threaded securing bolt to engage the releasable anchor connector carried by the chest encircling strap of the upper body harness.

* * * * *